US011877957B2

(12) United States Patent
Arba-Mosquera et al.

(10) Patent No.: US 11,877,957 B2
(45) Date of Patent: Jan. 23, 2024

(54) METHOD FOR CONTROLLING AN EYE SURGICAL LASER AND TREATMENT DEVICE

(71) Applicant: SCHWIND EYE-TECH-SOLUTIONS GMBH, Kleinostheim (DE)

(72) Inventors: Samuel Arba-Mosquera, Aschaffenburg (DE); Nico Triefenbach, Mainaschaff (DE); Mario Shraiki, Stockstadt (DE)

(73) Assignee: SCHWIND EYE-TECH-SOLUTIONS GMBH, Kleinostheim (DE)

( * ) Notice: Subject to any disclaimer, the term of this patent is extended or adjusted under 35 U.S.C. 154(b) by 4 days.

(21) Appl. No.: 16/791,190

(22) Filed: Feb. 14, 2020

(65) Prior Publication Data

US 2020/0261272 A1 Aug. 20, 2020

(30) Foreign Application Priority Data

Feb. 15, 2019 (DE) ..................... 10 2019 103 848.0

(51) Int. Cl.
*A61F 9/008* (2006.01)
(52) U.S. Cl.
CPC ............... *A61F 9/00825* (2013.01); *A61F 2009/00872* (2013.01)
(58) Field of Classification Search
CPC ................. A61F 9/00825; A61F 2009/00872
See application file for complete search history.

(56) References Cited

U.S. PATENT DOCUMENTS 6,110,166 A * 8/2000 Juhasz ............... A61F 9/00827
606/5
6,325,792 B1 12/2001 Swinger et al.
(Continued)

FOREIGN PATENT DOCUMENTS

DE 10 2007 019 814 A1 10/2008
DE 10 2007 053 283 A1 5/2009

OTHER PUBLICATIONS

Extended European Search Report dated Jul. 3, 2020 in corresponding European Application No. 20 155 996.0.
(Continued)

*Primary Examiner* — Mallika D Fairchild
*Assistant Examiner* — Naveed R. Kolia
(74) *Attorney, Agent, or Firm* — MEDLER FERRO WOODHOUSE & MILLS PLLC

(57) ABSTRACT

A method is disclosed for controlling an eye surgical laser for the separation of a volume body with predefined interfaces from a human or animal cornea. The method includes controlling the laser by means of a control device such that it emits pulsed laser pulses in a predefined pattern into the cornea, wherein the interfaces of the volume body to be separated are defined by the predefined pattern and a surface of the cornea and the interfaces located in the cornea are generated by photodisruption. A treatment device is also disclosed that includes at least one eye surgical laser for the separation of a predefined corneal volume with predefined interfaces of a human or animal eye by photodisruption, and at least one control device for the laser or lasers, which is formed to execute the steps of the method.

15 Claims, 2 Drawing Sheets

(56) References Cited

U.S. PATENT DOCUMENTS

| | | | |
|---|---|---|---|
| 2003/0212387 A1* | 11/2003 | Kurtz | A61F 9/00836 606/4 |
| 2004/0243112 A1 | 12/2004 | Bendett et al. | |
| 2006/0155265 A1 | 7/2006 | Juhasz et al. | |
| 2009/0187172 A1* | 7/2009 | Ruiz | A61F 9/00831 606/5 |
| 2010/0331830 A1 | 12/2010 | Bischoff et al. | |
| 2015/0374549 A1* | 12/2015 | Scott | A61F 9/013 606/5 |
| 2019/0015250 A1 | 1/2019 | Rathjen | |

OTHER PUBLICATIONS

Office Action dated Sep. 18, 2023 in corresponding Chinese Appl. No. 202010093066.5.

\* cited by examiner

METHOD FOR CONTROLLING AN EYE SURGICAL LASER AND TREATMENT DEVICE

FIELD

The present invention relates to a method for controlling an eye surgical laser for the separation of a volume body with predefined interfaces from a human or animal cornea. Furthermore, the invention relates to a treatment device with at least one eye surgical laser for the separation of a predefined corneal volume with predefined interfaces of a human or animal eye by means of photodisruption and at least one control device for the laser or lasers as well as to a computer program, a computer-readable medium, and a method for the separation of a volume body with predefined interfaces from a human or animal cornea.

BACKGROUND

Devices and methods for controlling a photoablative ophthalmologic laser are known. Thus, the international patent application WO 02/22003 describes a device for determining an area of corneal tissue to be ablated, wherein the volume of the tissue to be ablated is determined with the aid of a pachymetric measurement of the corresponding area of the cornea to be ablated. Therein, the determined pachymetric data serves for producing a bed within the cornea for receiving a corresponding donor cornea. U.S. Pat. No. 6,551,306 also describes a method and a device for surveillance the depth ablation on the cornea. Based on pachymetric data, a corresponding laser is controlled and supervised during a surgery.

However, it is disadvantageous in these known methods and devices that the entire volume body is evaporated by means of laser energy in the known ablative methods and devices. This requires relatively long treatment times on the one hand, a relatively high energy input by the laser into the cornea is effected on the other hand. In particular, the latter can result in complications in the removal of the predetermined volume body of the cornea. These disadvantages of known photoablative lasers, for example of excimer lasers, which predominantly emit in the ultraviolet range, could not yet be satisfactorily solved heretofore.

Therefore, it is the object of the present invention to provide a method and a treatment device for controlling an eye surgical laser for the separation of a volume body with predefined interfaces from a human or animal cornea, by which the disadvantages of the prior art are overcome.

SUMMARY

A generic method, a generic treatment device, a computer program, a computer-readable medium, and a method as described herein serve to solve this object.

Advantageous configurations with convenient developments of the invention are specified throughout the specification, wherein advantageous configurations of the method are to be regarded as advantageous configurations of the treatment device, of the computer program and of the computer-readable medium, and of a method for the separation of a volume body with predefined interfaces from a human or animal cornea, and vice versa.

A first aspect of the invention relates to a method for controlling an eye surgical laser for the separation of a volume body with predefined interfaces from a human or animal cornea. Therein, the method according to the invention comprises controlling the laser by means of a control device such that it emits pulsed laser pulses in a predefined pattern into the cornea, wherein the interfaces of the volume body to be separated are defined by the predefined pattern and a surface of the cornea, and the interfaces located in the cornea are generated by means of photodisruption. In that the volume body to be separated is only described and defined by the interfaces and these interfaces are generated by means of photodisruption, a full-area or full-volume ablation of the volume body can be omitted. Only the interfaces are generated by means of photodisruption such that the predefined volume body can subsequently be removed from the cornea. It is also to be understood by the term "interfaces" that the volume body can optionally be defined and separated by means of a single interface located in the cornea and the surface of the cornea. By the method according to the invention, the treatment duration for the separation of the volume body is shortened on the one hand, the energy input into the cornea of the patient is also significantly reduced on the other hand. Complications, which could in particular arise by an increased energy input into the cornea, are reliably prevented.

Therein, according to the invention, the surface of the cornea is a surface of the eye artificially generated by means of ablation or displacement of an uppermost corneal layer and/or by means of production of a corneal flap. Thereby, the method according to the invention is usable for a plurality of methods in the correction of visual disorders of the eye. In particular in the photorefractive keratectomy (PRK), in the epithelial laser-assisted keratomileusis (LASIK), the epithelial laser-assisted in-situ keratomileusis (Epi-LASIK) or the transepithelial photorefractive keratectomy (Trans-PRK), the method according to the invention for controlling an eye surgical laser can be used. It is a method, in which a tissue ablation occurs on an artificially generated corneal surface among other things. In contrast to the known method for tissue ablation of the artificial corneal surface, however, the laser is controlled such that a full-area ablation of a predefined volume body of the cornea is not effected in the method according to the invention, but the volume body is defined by the mentioned interfaces and the interfaces located in the cornea are generated by means of photodisruption.

Therein, there is the possibility that the laser is controlled such that the predefined pattern is processed starting from a interface of the volume body spaced from the surface of the cornea in the direction of the surface of the cornea. However, there is also the possibility that the laser is controlled such that the predefined pattern is processed starting from the surface of the cornea in the direction of said interface of the volume body spaced from the surface of the cornea. Advantageously, it can be decided, in which order the interfaces of the volume body to be separated are processed, corresponding to the topographic and/or pachymetric configurations of the cornea to be treated.

In further advantageous configurations of the method according to the invention, the interface spaced from the surface of the cornea extends substantially transversely to an optical axis of the eye. By the term "transversely", it is therein not to be understood that this interface always has to extend perpendicularly to the optical axis of the eye. Rather, it is to be understood by the term "transversely" that the corresponding interface can impinge on the optical axis at very different angles. Thus, the interface extending substantially transversely to the optical axis of the eye can lie on the optical axis at an angle between 45° and 135°. Furthermore, this interface can be formed at least partially straight and/or curved and/or wave-like and/or serrated and/or smooth. Other topographic configurations of the interface transverse to the optical axis of the eye as well as the lateral interfaces adjoining to this interface, which also serve as interfaces for defining the volume body, are also conceivable.

In further advantageous configurations of the method according to the invention, the laser is controlled such that the predefined pattern is at least partially circularly and/or spirally ablated. Therein, the start of the photodisruption can be effected by the individual laser pulses in the center of the respective interface or also at the edge of the respective interface.

In further advantageous configurations of the method according to the invention, the predefined pattern is defined based on one or more control datasets, wherein the control dataset or datasets include control data for positioning and/or for focusing individual laser pulses in the cornea. The determination of the control datasets is known and in particular results from the topographic and/or pachymetric measurement of the cornea to be treated as well as the type and the extent of the visual disorder to be corrected.

In further advantageous configurations of the method according to the invention, the volume body to be separated is formed such that a refractive correction of the eye is effected by the removal of the volume body. Furthermore, there is the possibility that the interface, which is substantially transverse to the optical axis of the eye, is generated immediately above, below or within the Bowman's membrane or crossing the Bowman's membrane. The mentioned visual disorders of the eye can be myopia, hyperopia, presbyopia, astigmatism or also other visual disorders of the eye.

In further advantageous configurations of the method according to the invention, the control device is formed such that the laser emits laser pulses in a wavelength range between 300 nm and 1400 nm, preferably between 900 nm and 1200 nm, at a respective pulse duration between 1 fs and 1 ns, preferably between 10 fs and 10 ps, and a repetition frequency of greater than 10 KHz, preferably between 100 KHz and 100 MHz. Such lasers are already used for photodisruptive methods in the eye surgery. Thus, EP 2 211 803 B1 for example describes a corresponding femto-second laser, which is used for producing a so-called lenticule, that is a lens-like volume body, within the cornea. The thus produced lenticule is subsequently removed from the cornea via an incision in it. However, the use of such photodisruptive lasers instead of ablatively effective lasers in the photorefractive keratectomy, that is in methods entailing an ablation of the corneal surface, is new and not known from the prior art. The use of photodisruptive lasers in the method according to the invention additionally has the advantage that the irradiation of the cornea does not have to be effected in a wavelength range below 300 nm. This range is subsumed by the term "deep ultraviolet" in the laser technology. Thereby, it is advantageously avoided that an unintended damage to the cornea is effected by these very short-wavelength and high-energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that high cutting precision in generating the interface(s) is ensured.

A second aspect of the present invention relates to a treatment device with at least one eye surgical laser for the separation of a predefined corneal volume with predefined interfaces of a human or animal eye by means of photodisruption and at least one control device for the laser or the lasers, which is formed to execute the steps of the method according to the first aspect of the invention. The treatment device according to the invention allows that the disadvantages occurring in the use of usual ablative treatment devices, namely relatively long treatment times and a relatively high energy input by the laser into the cornea, are reliably avoided. These advantages are in particular achieved by the formation of the eye surgical laser as a photodisruptive laser.

Therein, the laser is suitable to emit laser pulses in a wavelength range between 300 nm and 1400 nm, preferably between 900 nm and 1200 nm, at a respective pulse duration between 1 fs and 1 ns, preferably between 10 fs and 10 ps, and a repetition frequency of greater than 10 KHz, preferably between 100 KHz and 100 MHz.

In further advantageous configurations of the treatment device according to the invention, the control device includes at least one storage device for at least temporary storage of at least one control dataset, wherein the control dataset or datasets include control data for positioning and/or for focusing individual laser pulses in the cornea; and comprises at least one beam device for beam guidance and/or for beam shaping and/or for beam deflection and/or for beam focusing of a laser beam of the laser. Therein, the mentioned control datasets are usually generated based on a measured topography and/or pachymetry of the cornea to be treated and the type of the visual disorder of the eye to be corrected.

Further features and the advantages thereof can be taken from the descriptions of the first inventive aspect, wherein advantageous configurations of each inventive aspect are to be regarded as advantageous configurations of the respectively other inventive aspect.

A third aspect of the invention relates to a computer program including commands, which cause the treatment device according to the second inventive aspect to execute the method steps according to the first inventive aspect. A fourth aspect of the invention relates to a computer-readable medium, on which the computer program according to the third inventive aspect is stored. Further features and the advantages thereof can be taken from the descriptions of the first and the second inventive aspect, wherein advantageous configurations of each inventive aspect are to be regarded as advantageous configurations of the respectively other inventive aspect.

A further, fourth aspect of the invention relates to a method for separating a volume body with predefined interfaces from a human or animal cornea, comprising: controlling the laser by means of a control device such that it emits pulsed laser pulses in a predefined pattern into the cornea, wherein the interfaces of the volume body to be separated are defined by the predefined pattern and a surface of the cornea, and the interfaces located in the cornea are generated by means of photodisruption, and wherein the surface of the cornea is a surface of the eye artificially generated by means of ablation or displacement of an uppermost corneal layer and/or by means of production of a corneal flap.

The method according to the invention is usable for a plurality of methods in the correction of visual disorders of the eye. In particular, in the photorefractive keratectomy (PRK), in the epithelial laser-assisted keratomileusis (LASIK), the epithelial laser-assisted in-situ keratomileusis (Epi-LASIK) or the transepithelial photorefractive keratectomy (Trans-PRK), the method according to the invention can be used. It is a method, in which a tissue ablation occurs on an artificially generated corneal surface among other things. In contrast to the known method for tissue ablation of the artificial corneal surface, however, the laser is controlled such that a full-area ablation of a predefined volume body of the cornea is not effected in the method according to the invention, but the volume body is defined by the mentioned interfaces and the interfaces located in the cornea are generated by means of photodisruption.

Furthermore, the laser can be controlled such that the predefined pattern is processed starting from an interface of the volume body spaced from the surface of the cornea in the direction of the surface of the cornea. However, it is also possible that the laser is controlled such that the predefined pattern is processed starting from the surface of the cornea in the direction of an interface of the volume body spaced from the surface of the cornea.

In the method according to the invention, the volume body to be separated can be formed such that a correction of visual disorders of the eye is effected by the removal of the volume body. There is also the possibility that the posterior interface of the volume body is generated substantially transversely to the optical axis of the eye immediately above, below or within the Bowman's membrane or crossing the Bowman's membrane.

Further features and the advantages thereof can be taken from the descriptions of the first, the second and the third inventive aspect, wherein advantageous configurations of each inventive aspect are to be regarded as advantageous configurations of the respectively other inventive aspect.

Further features of the invention are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

DETAILED DESCRIPTION

Figure 1:
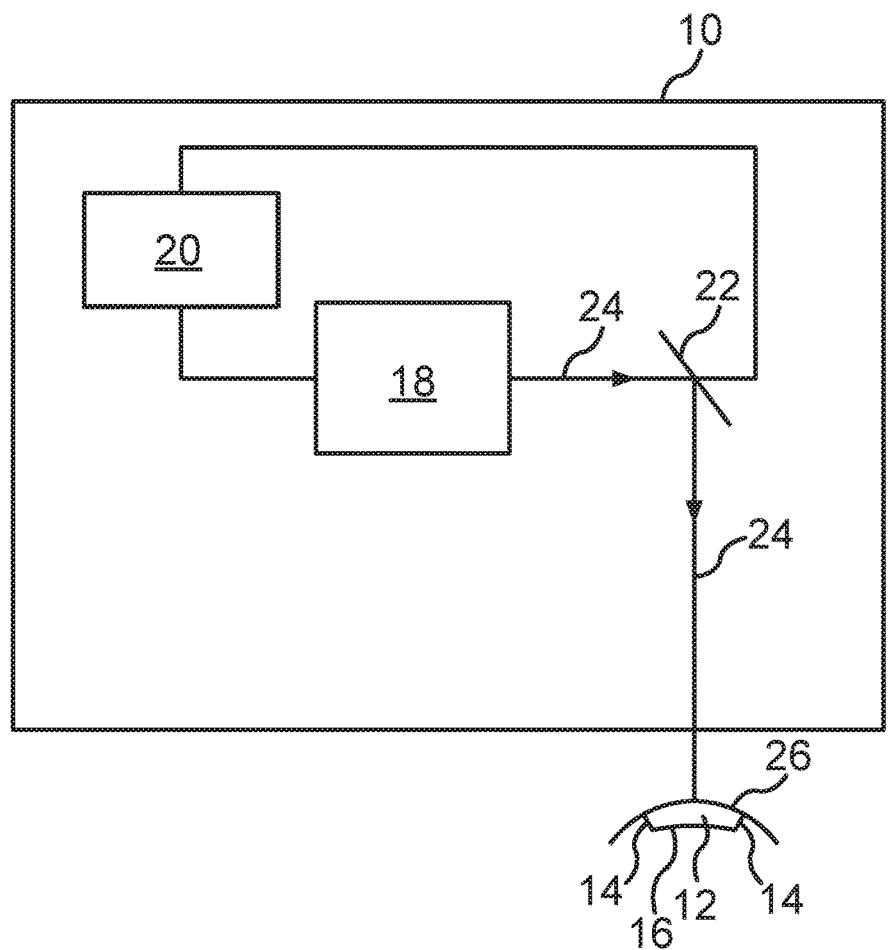
FIG. 1 a schematic representation of a treatment device according to the invention.

FIG. 1 shows a schematic representation of a treatment device 10 with an eye surgical laser 18 for the separation of a predefined corneal volume or volume body 12 with predefined interfaces 14, 16 of a cornea of a human or animal eye by means of photodisruption. One recognizes that a control device 20 for the laser 18 is formed besides the laser 18 such that it emits pulsed laser pulses in a predefined pattern into the cornea, wherein the interfaces 14, 16 of the volume body 12 to be separated are defined by the predefined pattern and a surface 26 of the cornea and the interfaces 14, 16 located in the cornea are generated by means of photodisruption.

Furthermore, one recognizes that the laser beam 24 generated by the laser 18 is deflected in the direction of the surface 26 of the cornea by means of a beam device 22, namely a beam deflection device, such as for example a scanner. The beam deflection device 22 is also controlled by the control device 20 to generate the mentioned predefined pattern in the cornea.

The illustrated laser 18 is a photodisruptive laser, which is formed to emit laser pulses in a wavelength range between 300 nm and 1400 nm, preferably between 900 nm and 1200 nm, at a respective pulse duration between 1 fs and 1 ns, preferably between 10 fs and 10 ps, and a repetition frequency of greater than 10 KHz, preferably between 100 KHz and 100 MHz.

In addition, the control device 20 comprises a storage device (not illustrated) for at least temporary storage of at least one control dataset, wherein the control dataset or datasets include control data for positioning and/or for focusing individual laser pulses in the cornea. The position data and/or focusing data of the individual laser pulses are generated based on a previously measured topography and/or pachymetry of the cornea and the visual disorder of the eye to be corrected.

Figure 2A:
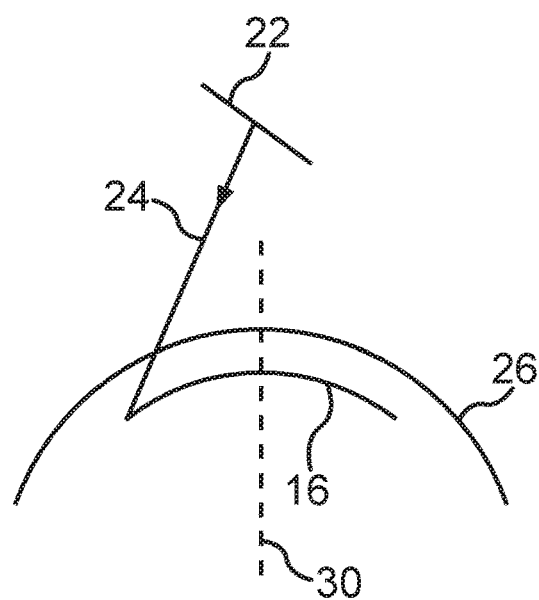
FIG. 2a a schematic diagram of the generation of a first interface according to a first embodiment of the method according to the invention.

FIG. 2a shows a schematic diagram of the generation of a first interface 16 according to a first embodiment of the present method. One recognizes that a first interface 16, which extends approximately transversely to an optical axis 30 of the eye, is generated within the cornea by means of the pulsed laser beam 24, which is directed in the direction of the cornea or the surface 26 of the cornea via the beam deflection device 22. In particular, the interface 16 is generated within the so-called stroma of the cornea. Therein, the interface 16 can for example be located immediately below the so-called Bowman's membrane.

One recognizes that the interface 16 is located approximately transversely to the optical axis 30, wherein the interface 16 is formed curved. The configuration of the interface 16 as well as the two lateral interfaces 14 (compare FIG. 2b) is determined by the type of the visual disorder of the eye to be corrected. Therein, the configuration of the interface 16 can in particular contribute to the correction of the visual disorder of the eye.

Figure 2B:
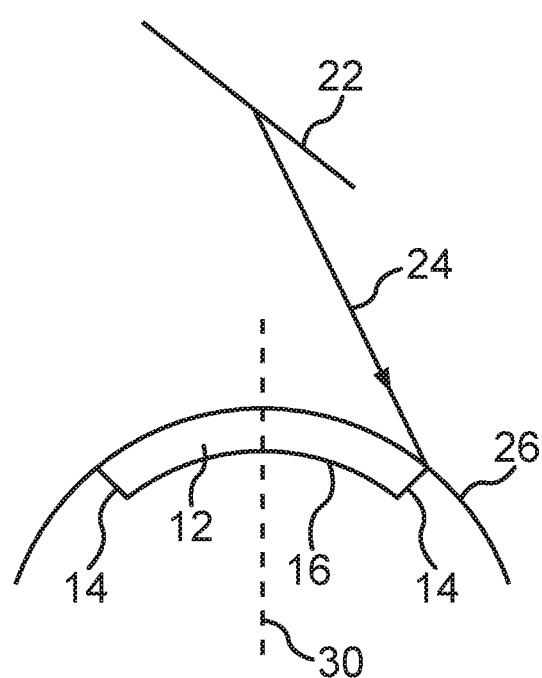
FIG. 2b a schematic diagram of the generation of a volume body to be separated according to the first embodiment of the method according to the invention.

FIG. 2b shows a schematic diagram of the generation of the volume body 12 to be separated according to the first embodiment of the present method described in FIG. 2a. One recognizes that the beam deflection device 22 controls the laser beam 24 such that the lateral interfaces 14 are processed starting from the interface 16 in the direction of the surface 26 of the cornea. Thereby, lateral incisions arise, which penetrate the ends of the interface 16 on the one hand and the surface 26 on the other hand to overall form the volume body 12 such that it can be separated from the cornea.

Figure 3:
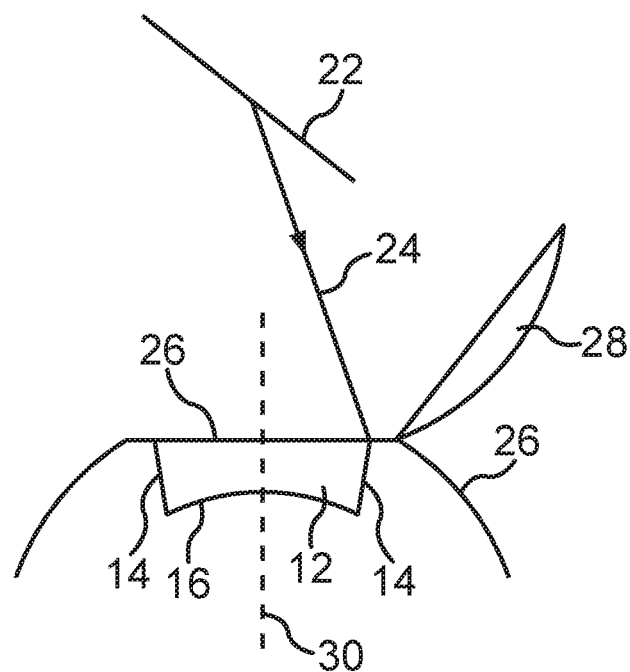
FIG. 3 a schematic diagram of the generation of a volume body to be separated according to a second embodiment of the method according to the invention.

FIG. 3 shows a schematic diagram of the generation of the volume body 12 to be separated according to a second embodiment of the present method. One recognizes that a so-called corneal flap 28 is generated before the generation of the interface 16 as well as the generation of the interfaces 14. Therein, the corneal flap 28 can be generated by means of a mechanical cutting device or also by means of a laser. For forming the corneal flap 28, the laser 18 can also be used. By folding back the corneal flap 28, it exposes a surface 26 of the cornea, from which the predefined volume body 12 with the interfaces 14, 16 can in turn be separated. After removing the volume body 12 from the cornea, the corneal flap 28 is again refolded and thus closes the cavity within the cornea generated by the removal of the volume body 12.

With respect to the explanation of the further features of FIG. 3, we make reference to the FIGS. 2a and 2b, wherein identical features are denoted by identical reference characters.

What is claimed is:

1. A method for controlling an eye surgical laser for the separation of a volume body with predefined interfaces from a human or animal cornea, comprising:
   controlling the laser by means of a control device such that it emits pulsed laser pulses in a predefined pattern into the cornea,
   wherein the interfaces of the volume body to be separated are defined by the predefined pattern and a surface of the cornea and the interfaces located in the cornea are generated by means of photodisruption,
   wherein the surface of the cornea is a surface of the eye artificially generated by means of ablation or displacement of an uppermost corneal layer and/or by means of production of a corneal flap,
   wherein the laser is controlled such that the predefined pattern is processed starting from the surface of the cornea in the direction of an interface of the volume body spaced from the surface of the cornea, and
   wherein the interface spaced from the surface of the cornea is generated transversely to the optical axis of the eye immediately above or within the Bowman's membrane or crossing the Bowman's membrane.

2. The method according to claim 1, wherein the interface spaced from the surface of the cornea extends transversely to an optical axis of the eye.

3. The method according to claim 2, wherein the interface spaced from the surface of the cornea is formed straight and/or curved and/or wave-like and/or serrated and/or smooth transversely to the optical axis of the eye.

4. The method according to claim 2, wherein the interface spaced from the surface of the cornea lies on the optical axis at an angle between 45° and 135° transversely to the optical axis of the eye.

5. The method according to claim 1, wherein the laser is controlled such that the predefined pattern is circularly and/or spirally ablated.

6. The method according to claim 1, wherein the predefined pattern is defined based on one or more control datasets, wherein the control dataset or datasets include control data for positioning and/or for focusing individual laser pulses in the cornea.

7. The method according to claim 1, wherein the volume body to be separated is formed such that a correction of visual disorders of the eye is effected by the removal of the volume body.

8. The method according to claim 1, wherein the control device is formed such that the laser emits laser pulses in a wavelength range between 300 nm and 1400 nm, at a respective pulse duration between 1 fs and 1 ns, and a repetition frequency of greater than 10 KHz.

9. A treatment device with at least one eye surgical laser for the separation of a predefined corneal volume with predefined interfaces from a human or animal eye by means of photodisruption and at least one control device for the laser or the lasers, which is formed to execute the steps of the method according to claim 1.

10. The treatment device according to claim 9, wherein the laser is suitable to emit laser pulses in a wavelength range between 300 nm and 1400 nm, at a respective pulse duration between 1 fs and 1 ns, and a repetition frequency of greater than 10 KHz.

11. The treatment device according to claim 9, wherein the control device
   comprises at least one storage device for the at least temporary storage of at least one control dataset, wherein the control dataset or datasets include control data for positioning and/or for focusing individual laser pulses in the cornea; and
   comprises at least one beam device for beam guidance and/or beam shaping and/or beam deflection and/or beam focusing of a laser beam of the laser.

12. A computer program including commands, which cause a treatment device with at least one eye surgical laser for the separation of a predefined corneal volume with predefined interfaces from a human or animal eye by means of photodisruption and at least one control device for the laser or the lasers to execute the method steps according to claim 1.

13. A non-transitory computer-readable medium, on which the computer program according to claim 12 is stored.

14. A method for separating a volume body with predefined interfaces from a human or animal cornea, comprising:
   controlling of a laser by means of a control device such that it emits pulsed laser pulses in a predefined pattern into the cornea,
   wherein the interfaces of the volume body to be separated are defined by the predefined pattern and a surface of the cornea and the interfaces located in the cornea are generated by means of photodisruption,
   wherein the surface of the cornea is a surface of the eye artificially generated by means of ablation or displacement of the uppermost corneal layer and/or by means of production of a corneal flap;
   wherein the laser is controlled such that the predefined pattern is processed starting from the surface of the cornea in the direction of an interface of the volume body spaced from the surface of the cornea, and
   wherein the interface spaced from the surface of the cornea is generated transversely to the optical axis of the eye immediately above or within the Bowman's membrane or crossing the Bowman's membrane.

15. The method according to claim 14, wherein the volume body to be separated is formed such that a correction of visual disorders of the eye is effected by the removal of the volume body.

* * * * *